(12) United States Patent
Watari et al.

(10) Patent No.: US 6,891,182 B2
(45) Date of Patent: May 10, 2005

(54) APPARATUS FOR AUTOMATICALLY DETECTING SIZE TO BE DETECTED AND AUTOMATIC ANALYZER USING THE SAME

(75) Inventors: Shigenori Watari, Hitachinaka (JP); Haruo Matsuoka, Saitama (JP)

(73) Assignees: Hitachi, Ltd., Tokyo (JP); Optoelectronics Co., Ltd., Saitama (JP)

( * ) Notice: Subject to any disclaimer, the term of this patent is extended or adjusted under 35 U.S.C. 154(b) by 56 days.

(21) Appl. No.: 10/091,425

(22) Filed: Mar. 7, 2002

(65) Prior Publication Data

US 2002/0134923 A1 Sep. 26, 2002

(30) Foreign Application Priority Data

Mar. 23, 2001 (JP) ........................................ 2001-085855

(51) Int. Cl.[7] ............................ G01N 21/86; G06K 7/10
(52) U.S. Cl. ........................... 250/559.19; 250/559.24; 250/568; 235/472.01; 235/462.01
(58) Field of Search ............................ 250/566, 568, 250/234, 235, 559.29, 559.24, 559.19, 559.25, 559.4, 221, 222.1, 577, 223 R, 223 B; 235/462.01, 375, 462.45, 462.49, 472.01, 472.03; 73/1.79, 1.81, 1.73

(56) References Cited

U.S. PATENT DOCUMENTS

| | | | | |
|---|---|---|---|---|
| 3,629,595 A | * | 12/1971 | Babunovic | |
| 4,179,707 A | * | 12/1979 | Sjodin | ...................... 348/142 |
| 4,852,029 A | * | 7/1989 | Pope et al. | .................... 702/41 |
| 5,400,476 A | * | 3/1995 | White | |
| 5,420,408 A | | 5/1995 | Weyrauch et al. | |
| 5,463,228 A | * | 10/1995 | Krause | |
| 5,672,317 A | | 9/1997 | Buhler et al. | |
| 5,764,785 A | * | 6/1998 | Jones et al. | |
| 5,818,976 A | | 10/1998 | Pasco et al. | |
| 5,828,449 A | * | 10/1998 | King et al. | |

FOREIGN PATENT DOCUMENTS

| | | |
|---|---|---|
| DE | 199 11 351 | 9/2000 |
| EP | 0 903 681 | 3/1999 |
| FR | 2 379 801 | 9/1978 |
| JP | 10-253910 | 9/1998 |
| JP | 11-083865 | 3/1999 |
| JP | 2000-105247 | * 4/2000 |
| JP | 2000-283824 | * 10/2000 |

* cited by examiner

Primary Examiner—Stephone B. Allen
(74) Attorney, Agent, or Firm—Mattingly, Stanger & Malur, P.C.

(57) ABSTRACT

In the automatic analyzer, the height of the test tubes is measured using the function of the optical information reader installed for discrimination of a sample. Various sensors installed so as to measure the height of the test tubes of the automatic analyzer can be omitted and decrease in cost, improvement of reliability, and improvement of maintenance capacity result.

14 Claims, 10 Drawing Sheets

FIG. 5
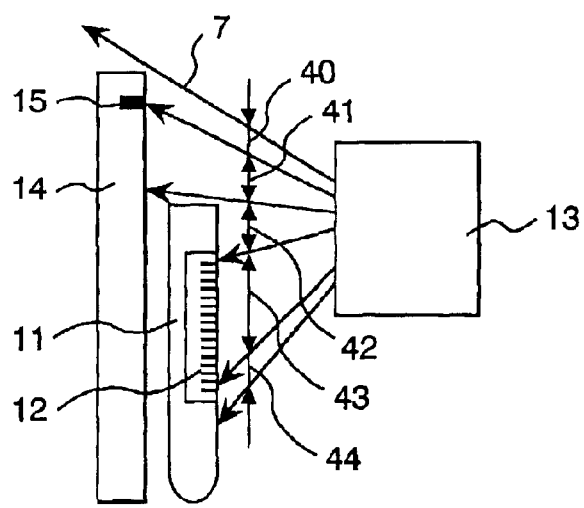
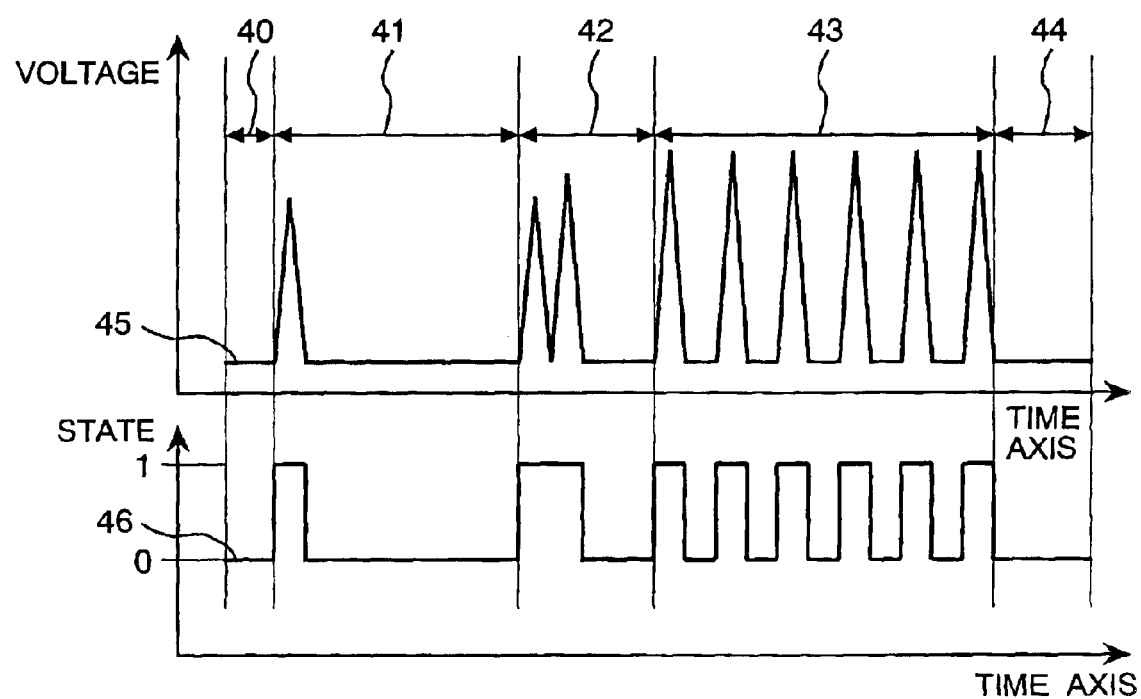

APPARATUS FOR AUTOMATICALLY DETECTING SIZE TO BE DETECTED AND AUTOMATIC ANALYZER USING THE SAME

BACKGROUND OF THE INVENTION

The present invention relates to an apparatus for automatically detecting the size to be detected and an automatic analyzer using it.

An apparatus for automatically detecting the size to be detected is required in various fields, for example, a semiconductor manufacturing device and an analyzer and well known as described in Japanese Laid-Open Patent Publication 2000-105247 and Japanese Laid-Open Patent Publication Hei 11-83865.

In a conventional automatic analyzer, to detect the height of a storage container such as a test tube or a sample cup for storing a specimen or a sample, as shown in FIG. 3, the light emission diodes 29 and the photo detectors (for example, phototransistors or photodiodes) 30 are arranged in an array state on the fixing plates 31 on both sides of a test tube, and changes by blocking off the light 32 generated by the light emission diodes by the test tube are detected by the photo detectors 30, and the height is measured.

The drive circuit 33 is connected to the light emission diodes 29 and the reception circuit is connected to the photo detectors 30. Further, by a laser displacement sensor, an ultrasonic displacement sensor, and a reflection type or transmission type laser discrimination sensor, the height of a test tube or the liquid level of a sample is detected. The aforementioned sensors are mounted separately from an optical information reader for reading the contents of a code pattern label attached to a container for storing a sample.

Furthermore, in Japanese Laid-Open Patent Publication 2000-283824, use of a CCD sensor for reading a code pattern provided in a container for storing a sample, obtaining information, and detecting the height of the container is described.

SUMMARY OF THE INVENTION

Generally, in a sampler unit of an automatic analyzer, as a container for storing a sample, a test tube (a blood collecting tube included) and a container for storing a very small quantity of sample which is called a sample cup are used.

These storage containers are loaded on a rack as shown in FIG. 4 and put in the sampler unit of an analyzer. However, a single test tube or a single sample cup may be loaded on a rack or a sample cup put on a test tube may be loaded on a rack.

The reason is that since a sample discrimination code pattern cannot be directly attached to the sample cup, the discrimination code pattern is attached to the test tube positioned below.

As mentioned above, in the states of a single test tube, a single sample cup, and a sample cup put on the upper part of a test tube, the liquid level of a sample stored in each container is greatly different. When a sample is to be poured at high speed in the sampler unit of the automatic analyzer, a high-speed operation of the sample arm is essential.

For that purpose, it is desirable to recognize the liquid level of the sample before executing the pouring operation and control the lowering speed of the sample arm. In the image processing using a displacement sensor using a laser or ultrasonic waves and a video camera, the height of a storage container can be detected with high precision. However, the sensor unit and operation control circuit unit are expensive and it is not preferable to apply them to an automatic analyzer.

Further, in a detector that light emission diodes and photo detectors are arranged in an array state as shown in FIG. 3, although the element price is inexpensive, a structure for fixing the elements is necessary, and the height to be judged is stepwise, and the detector cannot be made thin because the resolution is decided by the size of light emission diodes and photo detectors, and many drive circuits and detection circuits of the light emission diodes are necessary. Therefore, the height of test tubes which can be used is limited.

The automatic analyzer is described concretely above. However, the same may be said with general other dimension detectors.

An object of the present invention is to provide an apparatus for precisely detecting an optional length to be detected with an inexpensive system, for example, the length of a test tube.

One characteristic of the present invention is an apparatus for automatically detecting the size of a detection object having a detection object whose size is to be detected, a background panel which is arranged behind the detection object, has a reference line, and is longer than the detection object, and a controller for scanning the detection object and background panel from forth and automatically detecting the size of the detection object on the basis of an obtained signal.

Furthermore, the other characteristic is to propose an automatic analyzer using the aforementioned detector.

BRIEF DESCRIPTION OF THE DRAWINGS

FIG. 5 is an illustration for the operation of the embodiment.

DETAILED DESCRIPTION OF PREFERRED EMBODIMENTS OF THE INVENTION

The present invention will be explained in detail hereunder by referring to the embodiment. The present invention can be applied to various fields such that the size of a wafer is automatically detected by a semiconductor manufacturing device or the length of a test tube storing a sample is measured by an automatic analyzer. However, a case that the present invention is applied to an automatic analyzer will be explained hereunder.

Figure 1:
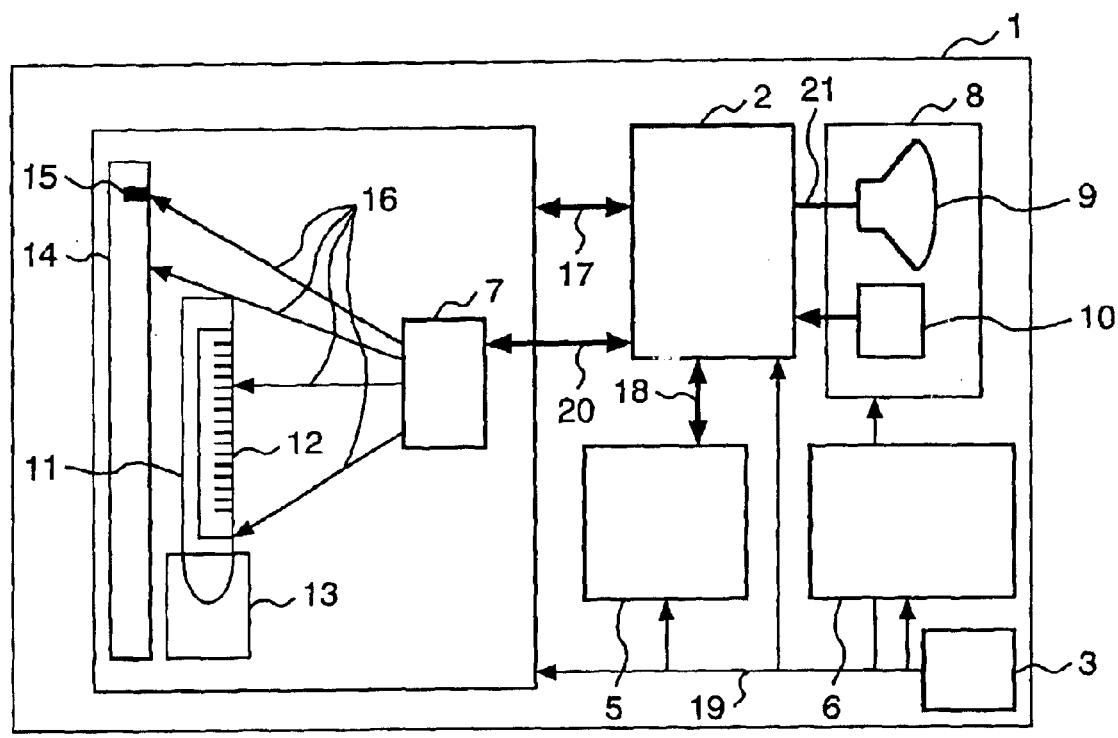
FIG. 1 is a schematic block diagram of an embodiment of an automatic analyzer to which the present invention is applied.
Figure 2:
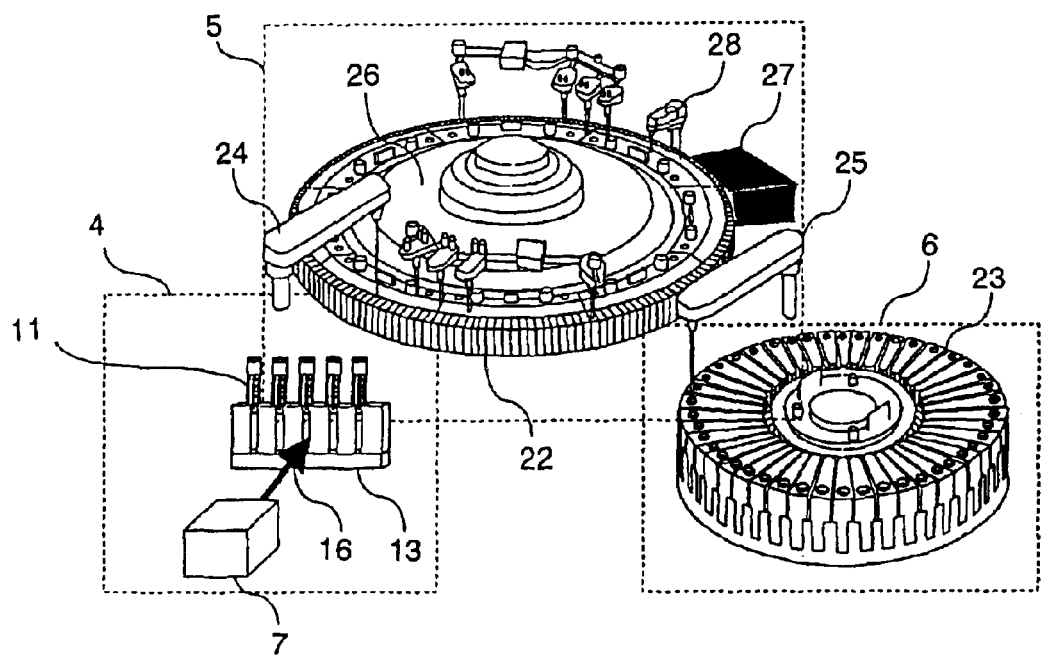
FIG. 2 is a top perspective view of the automatic analyzer shown in FIG. 1.
Figure 3:
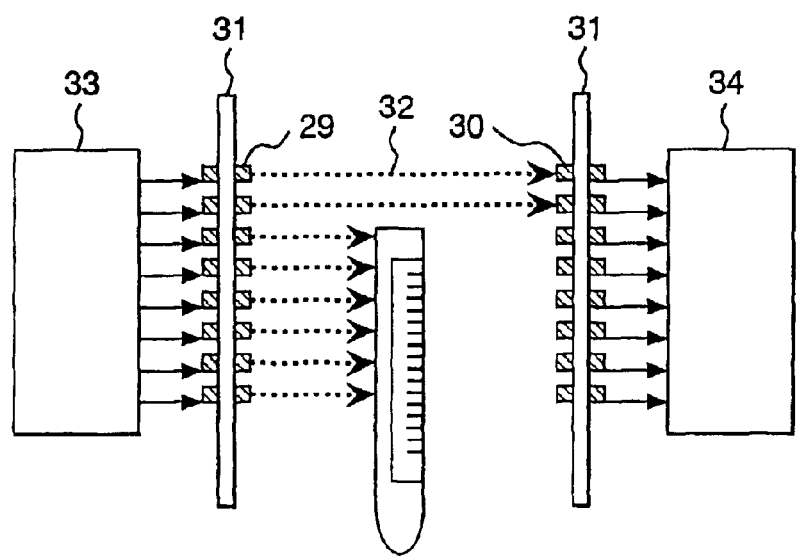
FIG. 3 is a schematic block diagram of a conventional detection example of container height.
Figure 4:
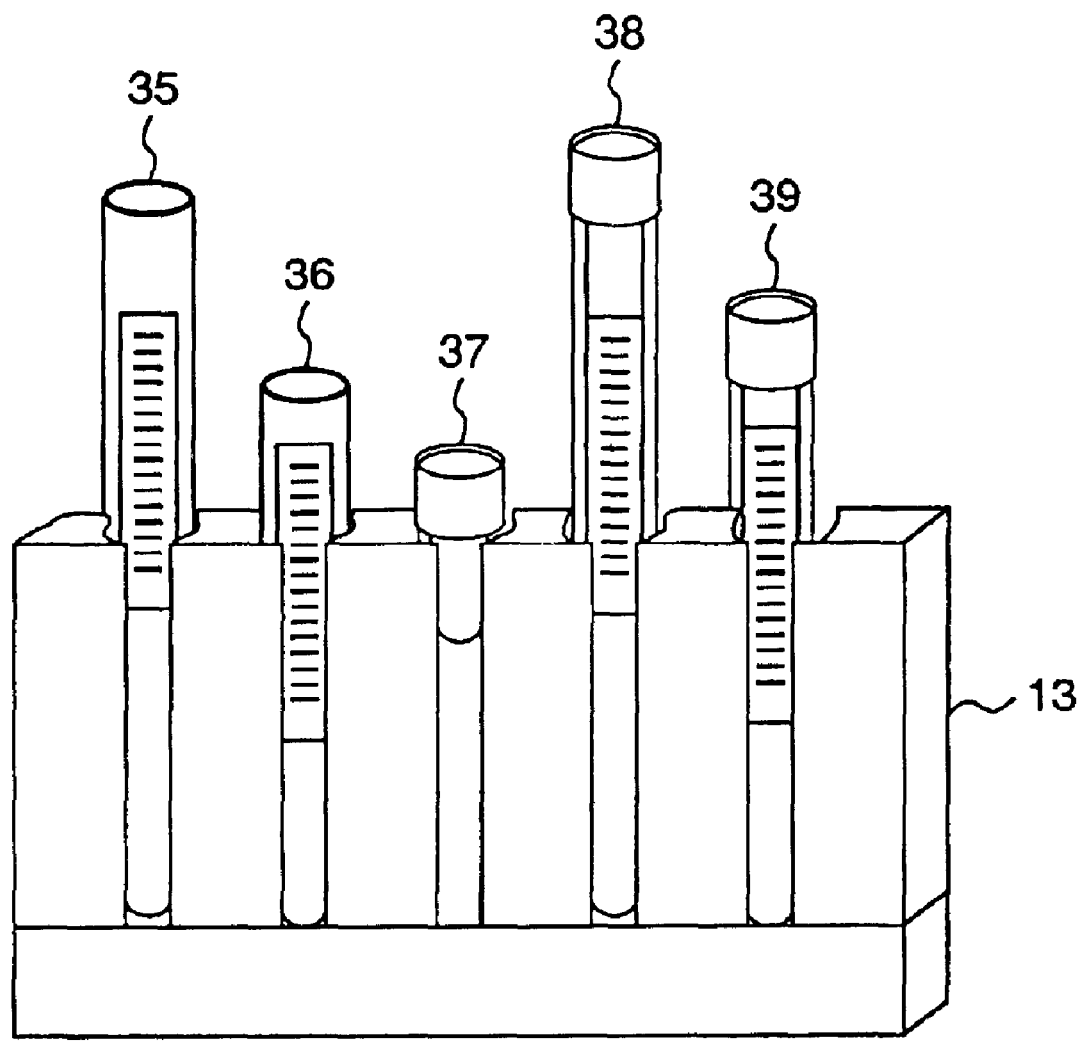
FIG. 4 is a schematic view of a concrete example of various storage containers.

FIGS. 1, 2, and 4 are schematic block diagrams of an embodiment of an automatic analyzer to which the present invention is applied. In FIG. 1, a controller 2 is composed of an information processor or a sequencer having an auxiliary storage unit such as an MPU, memory, I/O unit, communication circuit, or hard disk and processes or controls information necessary for the operation and analytical operation of the automatic analyzer.

A analytical unit 5, as shown in FIG. 2, is arranged on a moving reaction disk 26 for loading a plurality of reaction cells 22 which are containers for mixing a reagent and a sample and moving them at the same time, and measures the absorbance by a detector 27, and analyzes the components of the sample which is an analytical object.

A reagent storage unit 6 has a function for storing a reagent used for analysis, moving a necessary reagent to the position where the reagent can be sucked by a reagent probe 25, and keeping the reagent cool. A sampler unit 4 puts and stores a sample which is an analytical object in a test tube 11 and a sample cup 37 and the sampler 4 has a structure for moving a sample to be analyzed to the position where the sample is to be poured by a sample probe 24.

For the controller 2, the analytical unit 5, the reagent storage unit 6, and the sampler unit 4, the power necessary for the operation of each element is supplied from a power unit 3 in the apparatus. The power unit 3 in the apparatus changes and supplies the power to the voltage, current, and frequency necessary to each part in the apparatus.

The sample cup 37 is loaded on a rack 13 and moved to the pouring position, and the test tube 11 is attached with a code pattern 12 for the purpose of individual discrimination, and the contents of the code pattern 12 are read by an optical information reader 7.

In this embodiment, the optical information reader 7 adopting a scanning system by a laser is used. The read information of the code pattern 12 is transferred to the controller 2 via a code pattern communication line 20 and analysis of the analytical items in correspondence to the contents is started.

At the position where the optical information reader 7 reads the code pattern 12, this analyzer, as shown in FIG. 1, has a background panel 14 on the opposite side of the optical information reader 7 holding the test tube 11. The size of the background panel 14 is longer than the length of the test tube 11 which is a detection object.

On the background panel 14, for example, a black reference line 15 is arranged horizontally and when a laser beam 16 is irradiated to the code pattern 12 attached to the test tube 11 from the optical information reader 7, as shown in FIG. 5, the laser beam 16 is irradiated also to the background panel 14.

The optical information reader 7 detects the reference line 15 first. When the reader 7 detects the reference line 15, the reader 7 operates the internal timer or counter and then measures the time until the reader 7 detects scattered light from the upper end of the test tube 11 or the sample cup 37, that is, the time equivalent to the height detection period 41 shown in FIGS. 5 and 6.

The relative heights of the reference line 15 and the optical information reader 7 are respectively fixed in the analyzer, so that by the difference in height between the test tube 11 and the sample cup 37 positioned at the middle part, the aforementioned height detection period 41 is changed and the complementary value for the height of the test tube 11 and the sample cup 37 positioned at the middle part can be measured.

Thereafter, the optical information reader 7 passes the quiet period 42 and then reads the contents of the code pattern 12 attached for discrimination during the code pattern reading period 43. When the reading succeeds, it indicates that a test tube exists, so that assuming the time data in the height detection period 41 at the point of time as data for judging the height of the test tube 11, the optical information reader 7 transmits it to the controller 2 via the code pattern communication line 20.

The controller 2, in consideration of a difference between the respective apparatuses beforehand, prepares a comparison table between the time data in the height detection period 41, the height of various test tubes 11 and sample cups 37, and the height when they are combined and judges whether the time data in the height detection period 41 transmitted whenever necessary is the one for a long test tube 35, for a short test tube 36, for the sample cup 37, for a long test tube+sample cup 38, or a short test tube+sample cup 39.

In the preparation of the comparison table, in the adjustment process at the time of installation of the apparatus, start-up of the apparatus, or maintenance of the apparatus, the height of the test tube 11 to be used, the height of the sample cup 37 to be used, and the height when they are combined are read and prepared by the optical information reader 7 once and stored in the controller 2 as reference data, thus the effect by apparatus differences is reduced.

According to the embodiment of the present invention, by the optical information reader originally having only the function for reading he code pattern, the height of the sample storage container such as the test tube and sample cup can be measured, so that dedicated sensors for height measurement are not necessary and the cost is reduced. Further, adjustment of the dedicated sensors is not necessary and the maintenance capacity is improved. Furthermore, the number of parts is reduced and the reliability is improved.

Figure 6:
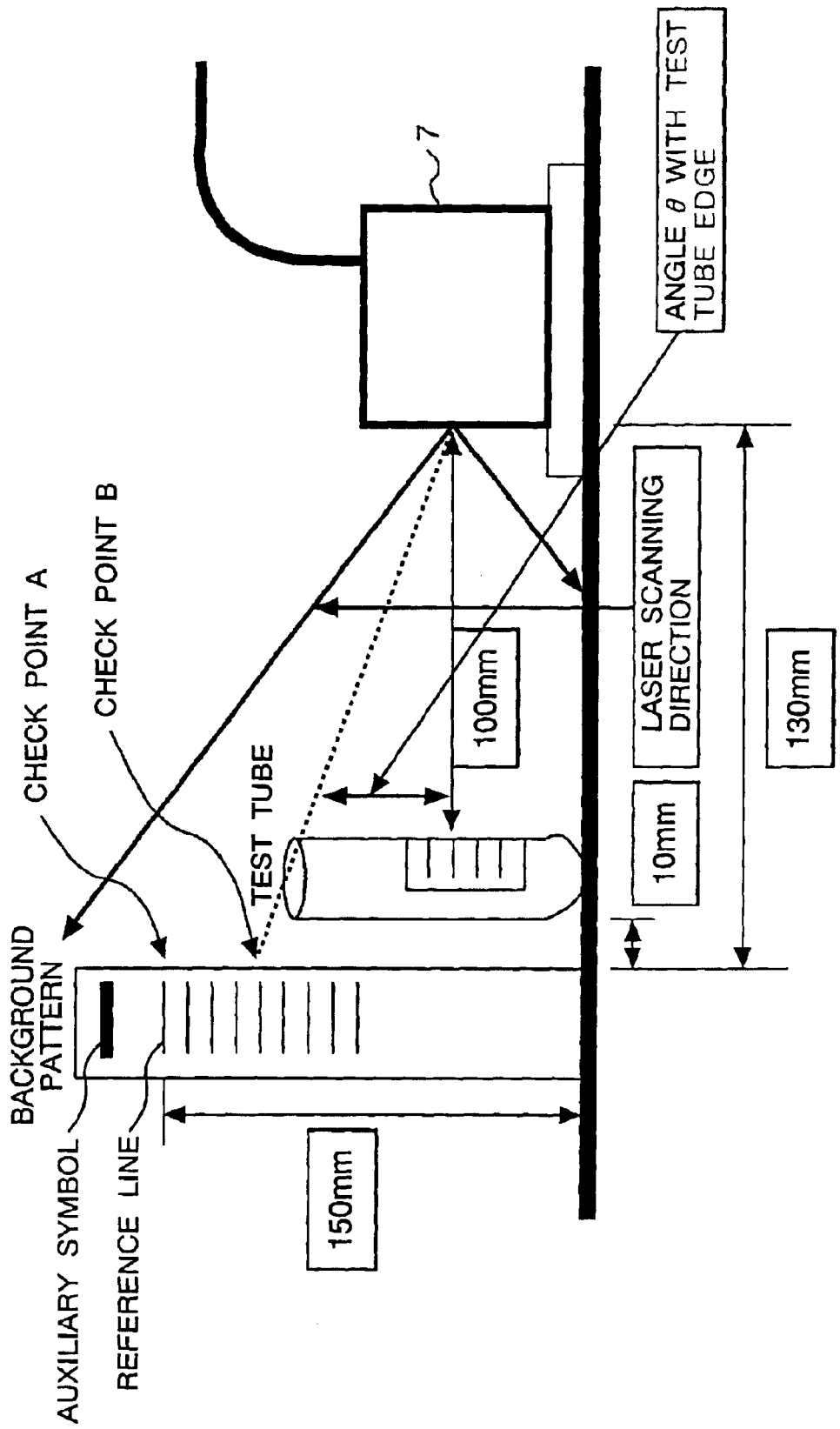
FIG. 6 is a schematic view showing an example of the background pattern.

When a plurality of bars are provided on the background panel 14 in addition to the reference line 15, the detection precision can be improved. FIG. 6 is a schematic view showing an example of a case that a plurality of bars are provided on the background panel as a background pattern and FIG. 7 is an illustration showing an enlarged part.

Furthermore, an auxiliary symbol is provided on the background panel 14. The auxiliary symbol is used to clearly indicate the position of the reference line 15 to the optical information reader 7 and improve the function thereof. Namely, the auxiliary symbol has a function for resetting the digitizer of the optical information reader 7. Further, by use of the auxiliary symbol, even when the optical information reader scans from above to below, a more excellent reading capacity can be obtained.

Figure 7:
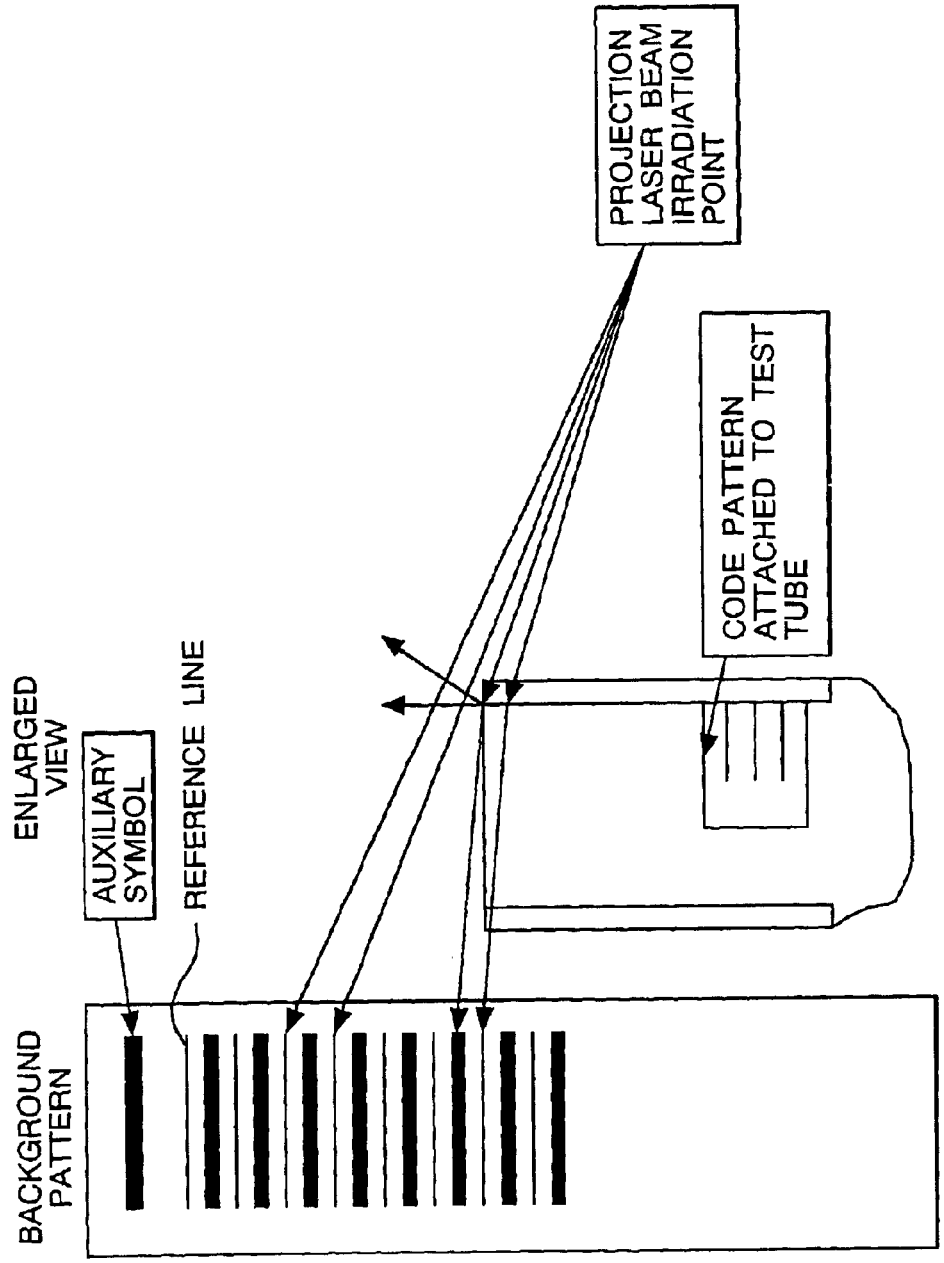
FIG. 7 is an illustration for an enlarged part of FIG. 6.

As shown in FIGS. 6 and 7, a projected laser beam is refracted and reflected at the edge of the test tube, so that the check point B is disordered by the obtained waveform. The disorder appears violently as the angle θ increases. The same may be said with light other than the laser beam, for example, LED light.

Figure 8:
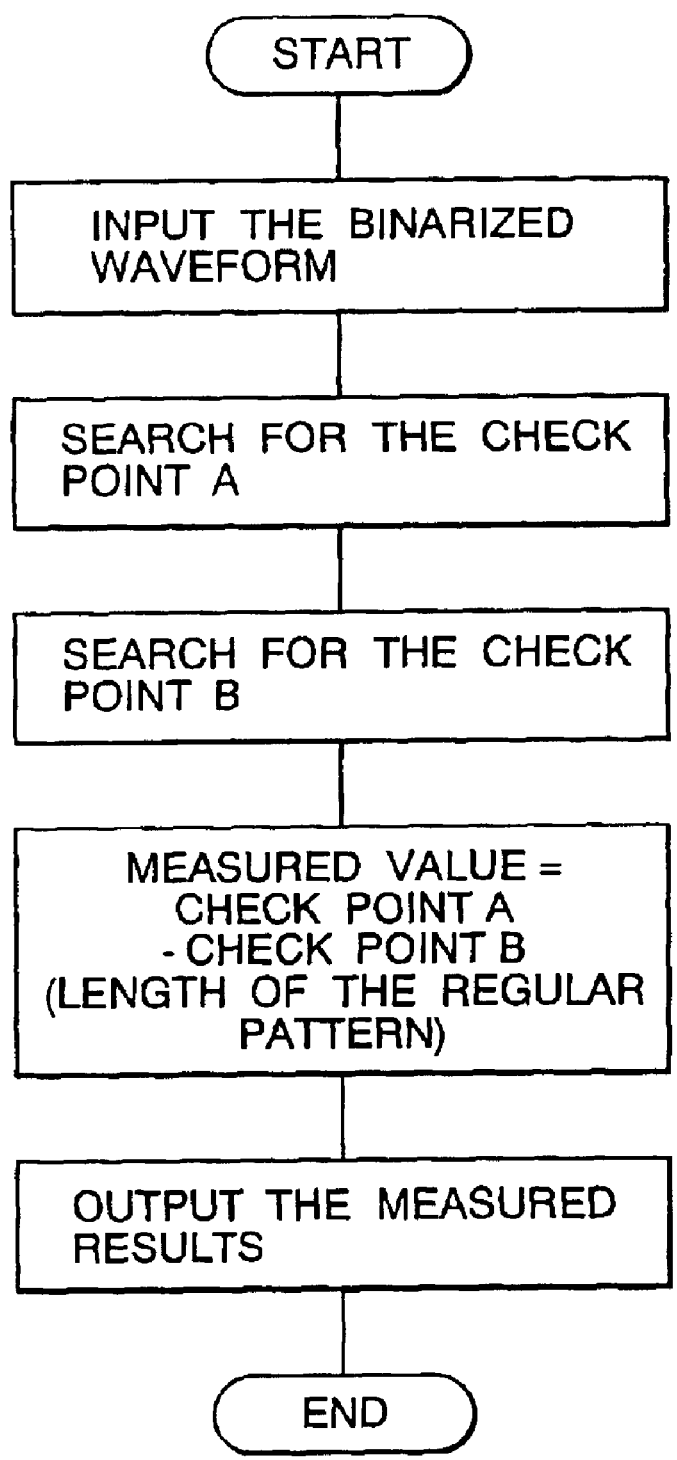
FIG. 8 is a measurement flow chart.

FIG. 8 is a flow chart when measurement is executed. The optical information reader 7 optically scans from below to above at a scan speed of 500 scan/s. A laser beam is projected and photo detector data is binarized (digitized) and transmitted to the controller 2.

Firstly, the check point A, that is, the top point (the top point of the part not interrupted by the test tube) of the background pattern is searched for. This point is indicated by the elapsed time (measurement unit: micro second) from the left start point of the binarized waveform.

Next, returned to the left from the check point A, the check point B is searched for. When the check point B is calculated from the check point A, the value is equivalent to the length of the test tube. When the output time is converted into length and subtracted from the length of the top point of the background pattern (reference line), the length of the test tube is obtained. When the measurement is repeated several times and the average is calculated, optical noise can be removed.

Figures 9A, 9B:
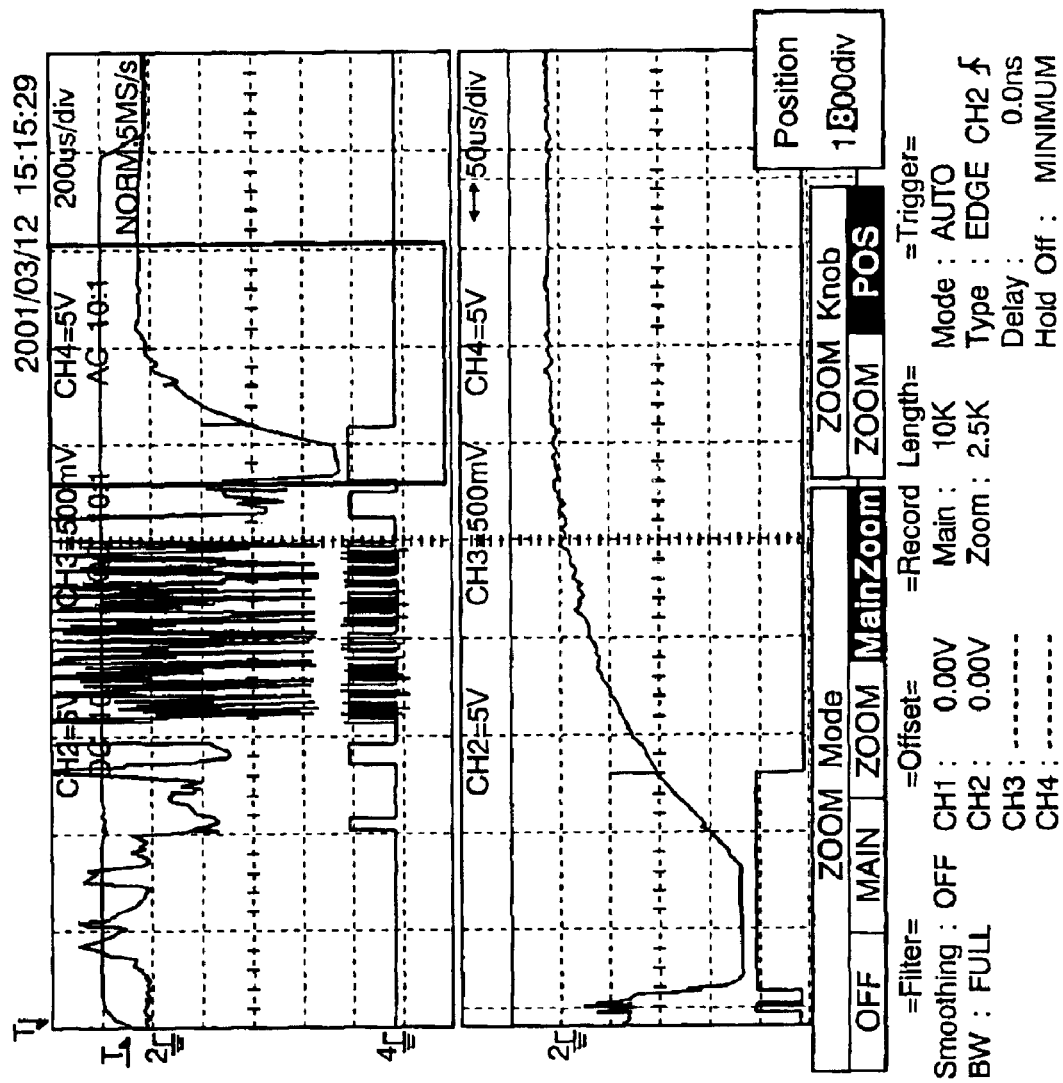
FIG. 9 shows cases that the background is black and no background is provided in the output waveform when the background pattern is changed.
Figures 10A, 10B:
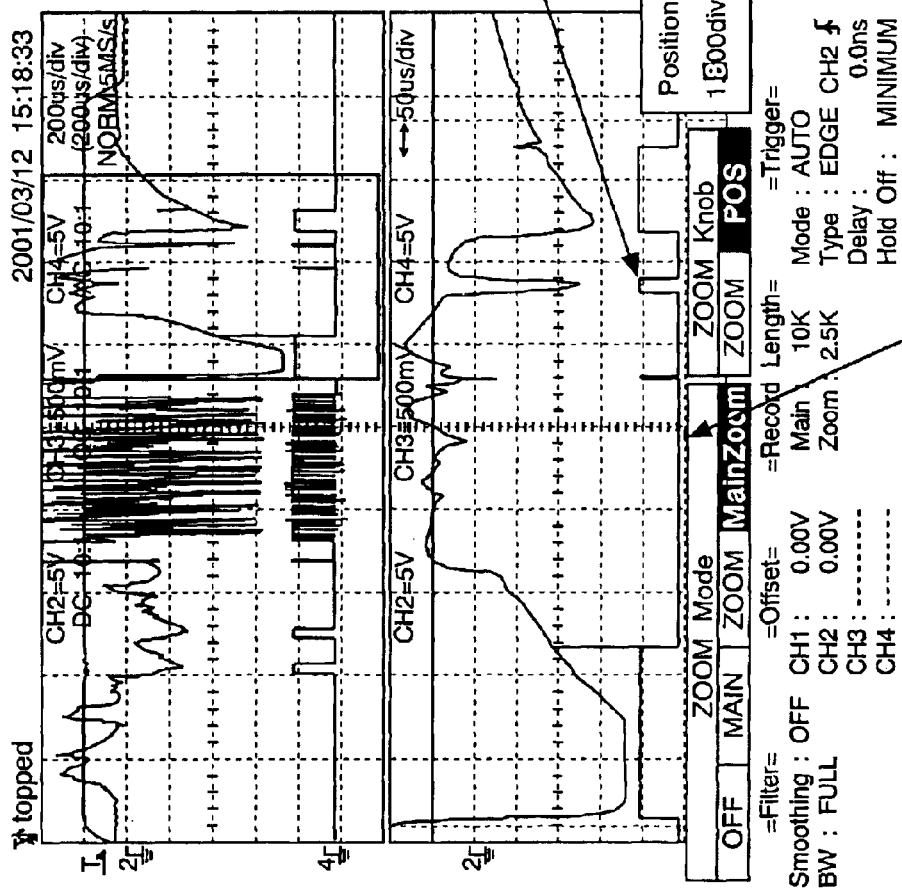
FIG. 10 shows a case that the background is white in the output waveform when the background pattern is changed.
Figures 11A, 11B:
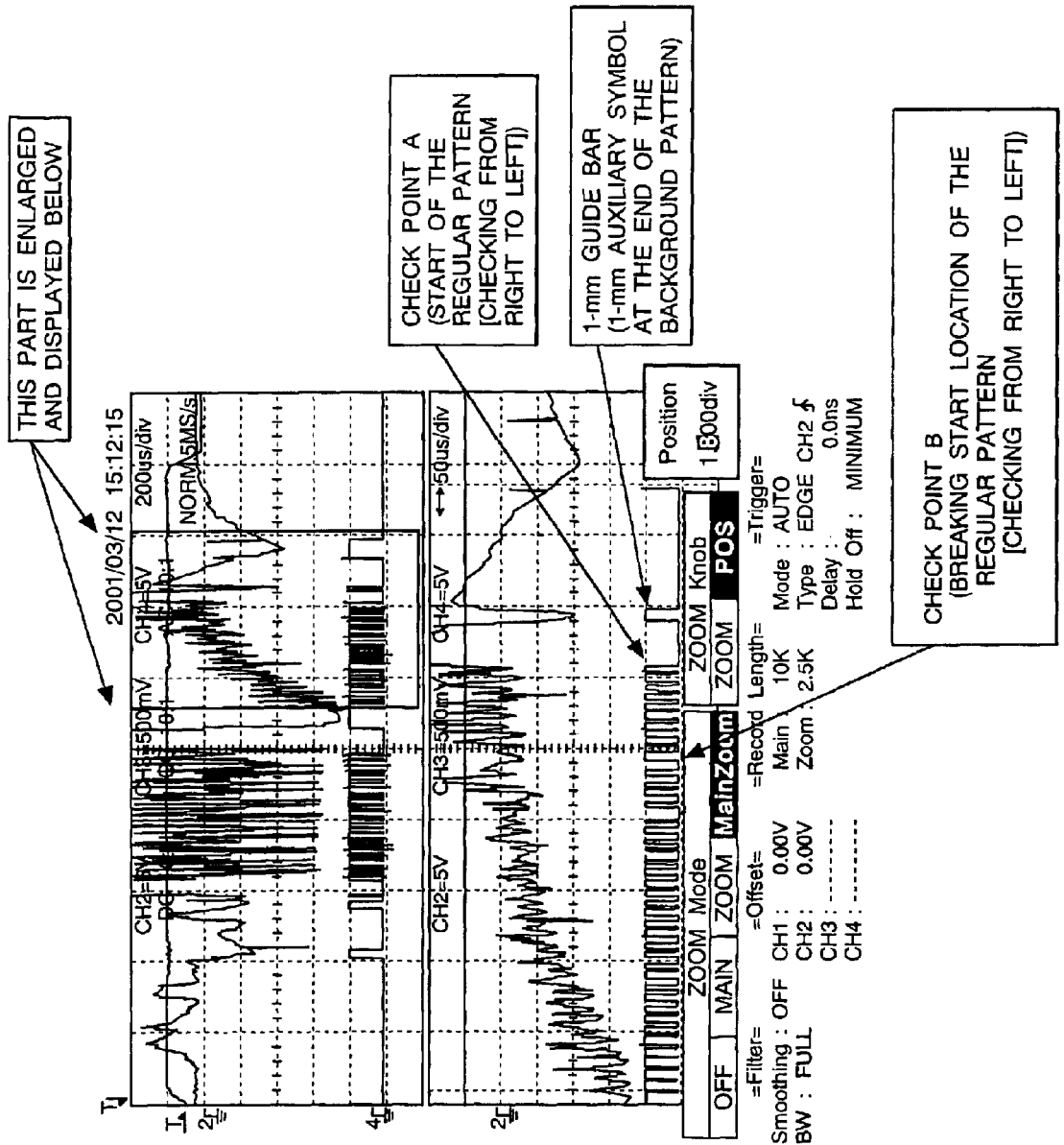
FIG. 11 shows a case that a code pattern is used for the background.

FIGS. 9 to 11 are drawings showing output waveforms when the background pattern is changed, and (A) is a whole diagram, and (B) is a partial enlarge diagram. The respective signal waveforms are a timing signal in the upper row, an analog waveform taken in by the scanner in the middle row, and a binarized signal waveform transmitted by the microcomputer in the lower row.

FIG. 9 shows cases that the background is black and no background is provided. The test tube which is a detection object is transparent, so that a waveform indicating a change point is not obtained. FIG. 10 shows a case that the background is white and a waveform at the edge of the test tube is obtained. However, the waveform is unstable, so that there is the possibility that a sufficient waveform may not be obtained due to the relative position of light projection and the shape of the test tube.

FIG. 11 shows a case that a code pattern is provided as a background pattern and the check points A and B are taken precisely.

The automatic size detection apparatus of the present invention can be applied to, in addition to the automatic analyzer explained above in detail, uses of automatically measuring the size and length of a body, for example, automatic detection of the size of a wafer in a semiconductor device. Particularly, when a code pattern is attached to a body, the code pattern information is read and the size of the body can be measured at the same time, so that an apparatus having a simple constitution for reading the size of a body and code pattern information can be provided.

As mentioned above, according to the present invention, the length of a detection object can be detected precisely.

What is claimed is:

1. An apparatus for automatically detecting a size of a detection object comprising:
   a background panel having a mark as a standard; and
   a controller arranged to control a bar code reader for performing an optical scan of said detection object and said background panel with said detection object arranged between said background panel and a scanning source, to read information encoded in a barcode pattern arranged on the detection object and to automatically detect the size of said detection object, on the basis of signals obtained by electrically converting scanning light of said optical scan of said barcode pattern and of a shortest scan from said mark to detection of said detection object.

2. An apparatus for automatically detecting a size of a detection object comprising:
   a background panel having a mark as a standard and a code pattern arranged along a length direction of said detection object when said detection object is arranged for scanning; and
   a controller arranged to control a code reader for performing an optical scan of said detection object and said background panel with said detection object arranged between said background panel and a scanning source, to read information encoded in said code pattern and to automatically detect the size of said detection object, on the basis of signals obtained by electrically converting scanning light of said optical scan of said code pattern and of a shortest scan from said mark to detection of said detection object.

3. An apparatus for automatically detecting a size of a detection object according to claim 2, wherein said code pattern is a bar code.

4. An automatic analyzer comprising:
   an analytical unit for analyzing components of a sample which is an analytical object using a reagent;
   a sampler unit for holding said sample and executing a pouring operation so as to transfer said sample of a volume necessary for analysis to said analytical unit;
   a controller for controlling said analytical unit and said sampler unit;
   a power unit for supplying power necessary for operations of said controller, said analytical unit, and said sampler unit to said respective units,
   an optical information reader for reading contents of a code pattern label attached to a container for storing said sample as an object of discrimination, including a background panel having a mark as a standard installed behind said container when said container is arranged between said background panel and a scanning source; and
   means for optically scanning said background panel and said code pattern by said optical information reader, measuring a height of said container with said code pattern attached on the basis of a signal obtained by electrically converting reflected light, and transmitting a result indicating said measured height of said container and discrimination information of said code pattern to said controller.

5. An automatic analyzer according to claim 4, wherein said background panel includes an auxiliary symbol in a neighborhood of said mark as a standard.

6. An automatic analyzer comprising:
   an analytical unit for analyzing components of a sample which is an analytical object using a reagent;
   a reagent container for storing said reagent;
   sampler unit for holding said sample and executing a pouring operation so as to transfer said sample of a volume necessary for analysis to said analytical unit;
   a controller composed of an electron circuit including an MPU, a memory, an I/O unit, and a sequencer for processing information, and a storage unit, for controlling said analytical unit and said sampler unit;
   a power unit for supplying power necessary for operations of said controller, said analytical unit, and said sampler unit to said respective units;
   an optical information reader for reading contents of a code pattern label attached to a container for storing said sample as an object of discrimination, including a background panel having a mark as a standard installed behind said container when said container is arranged between said background panel and a scanning source; and
   means for optically scanning said background panel and said code pattern by said optical information reader, measuring a height of said container with said code pattern attached on the basis of a signal obtained by electrically converting reflected light, and transmitting a result indicating said measured height of said container and discrimination information of said code pattern to said controller.

7. An automatic analyzer according to claim 6, wherein said background panel includes an auxiliary symbol in a neighborhood of said mark as a standard.

8. An apparatus for automatically detecting a size of a detection object, comprising:

a background panel having a mark as a standard;

a bar code reader which reads a code pattern arranged on said detection object by means of scanning light; and a controller arranged to control said barcode reader for performing an optical scan of said detection object and said background panel with said detection object arranged between said background panel and a scanning source, to read information encoded in said code pattern and to automatically detect the size of said detection object, on the basis of a signal obtained by electrically converting scanning light of said optical scan of said code pattern and of a shortest scan from said mark to detection of said detection object.

9. An apparatus for automatically detecting a size of a detection object, comprising:

a background panel having a mark as a standard and a code pattern arranged along a length direction of said detection object when said detection object is arranged for scanning;

an optical scanning information reader which reads the code pattern by means of scanning light; and a controller arranged to control an optical scan of said detection object and said background panel with said detection object arranged between said background panel and a scanning source and to automatically detect the size of said detection object on the basis of a signal obtained by electrically converting reflected light of a shortest scan from said mark to detection of said detection object, said controller controlling said optical information reader to scan optically said detection object.

10. An apparatus for automatically detecting a size of a detection object, comprising:

a background panel having a mark as a standard;

an optical information reader for reading contents of a code pattern label attached to said detection object for discrimination; and means for optically scanning said background panel and said code pattern by said optical information reader, measuring a size of said detection object on the basis of a signal obtained by electrically converting reflected light, of a shortest scan from said mark to detection of said detection object and transmitting a result indicating said measured size of said detection object and discrimination information of said code pattern to a controller.

11. An apparatus for automatically detecting a size of a detection object, comprising:

a background panel having a mark as a standard;

an optical scanning reader for performing an optical scan of said detection object, to which a code pattern is arranged along a length direction of the detection object, and said background panel with said detection object arranged between said background panel and a scanning source; and a controller arranged to control said optical scanning reader, to read information encoded in said code pattern and to automatically detect the size of said detection object, on the basis of signals obtained by electrically converting scanning light of the optical scan of said code pattern and of a shortest scan from said mark to detection of said detection object.

12. An apparatus for automatically detecting a size of a detection object, comprising:

a background panel having a mark as a standard and a barcode pattern arranged along a length direction of said detection object when said detection object is arranged for scanning;

a bar code reader for performing an optical scan of said detection object and said background panel with said detection object arranged between said background panel and a scanning source; and a controller arranged to control said bar code reader, to read information encoded in said barcode pattern and to automatically detect the size of said detection object on the basis of signals obtained by electrically converting scanning light of the optical scan of said barcode pattern and of a shortest scan from said mark to detection of said detection object.

13. An apparatus for automatically detecting a size of a detection object, comprising:

a background panel having a mark as a standard;

an optical scanning reader for performing an optical scan of said detection object, on which a code pattern is arranged, and said background panel with said detection object arranged between said background panel and a scanning source; and a controller arranged to control said optical scanning reader, to read information encoded in said code pattern and to automatically detect the size of said detection object, on the basis of signals obtained by electrically converting scanning light of the optical scan of said code pattern and of a shortest scan from said mark to detection of said detection object.

14. An apparatus for automatically detecting a size of a detection object, comprising:

a background panel having a mark as a standard and a barcode pattern arranged along a length direction of said detection object when said detection object is arranged for scanning;

a bar code reader for performing an optical scan of said detection object and said background panel with said detection object arranged between said background panel and a scanning source; and a controller arranged to control said bar code reader to read information encoded in said barcode pattern and to automatically detect the size of said detection object, on the basis of signals obtained by electrically converting scanning light of said optical scan of said barcode pattern and of a shortest scan from said mark to detection of said detection object.

* * * * *